Figure 1:
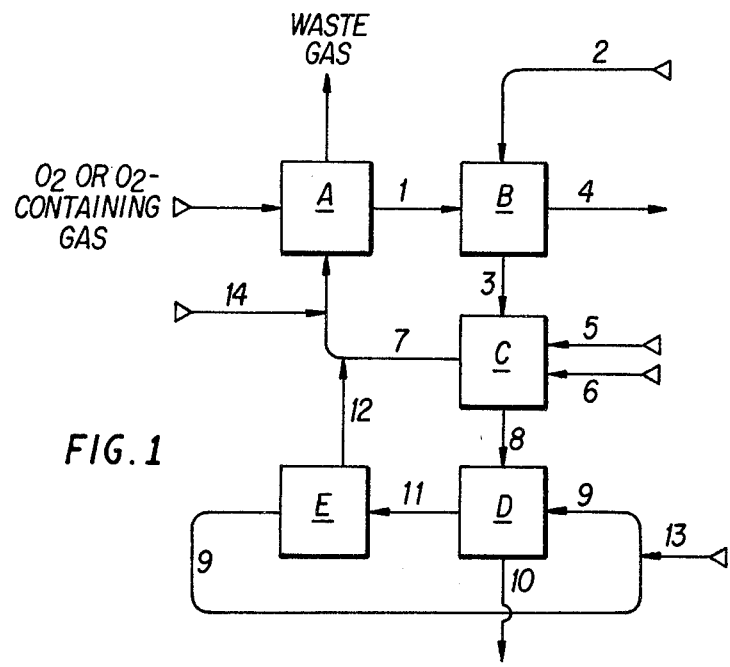

United States Patent [19]

Voges

[11] 4,271,321

[45] Jun. 2, 1981

[54] PROCESS FOR THE PREPARATION OF ARALIPHATIC DIHYDROPEROXIDES

[75] Inventor: Heinz W. Voges, Dorsten, Fed. Rep. of Germany

[73] Assignee: Chemische Werke Huls Aktiengesellschaft, Fed. Rep. of Germany

[21] Appl. No.: 82,661

[22] Filed: Oct. 9, 1979

[30] Foreign Application Priority Data

Oct. 9, 1978 [DE] Fed. Rep. of Germany ....... 2843857

[51] Int. Cl.³ .......................................... C07C 179/047
[52] U.S. Cl. .................................... 568/569; 568/568; 568/576; 568/577
[58] Field of Search ............... 568/564, 568, 577, 576, 568/569

[56] References Cited

U.S. PATENT DOCUMENTS

| | | | |
|---|---|---|---|
| 2,715,646 | 8/1955 | Hawkins et al. | 568/573 |
| 2,856,432 | 10/1958 | Conner | 568/565 |
| 2,856,433 | 10/1958 | Thompson | 568/565 |
| 2,915,557 | 12/1959 | Kreps et al. | 568/562 |
| 3,190,424 | 6/1965 | Sodomann et al. | 568/562 |
| 3,190,923 | 6/1965 | Sodomann et al. | 568/562 |
| 3,360,570 | 12/1967 | Bewley et al. | 568/565 |
| 3,911,020 | 10/1975 | Cooper | 568/565 |
| 3,978,138 | 8/1979 | Yanagihara et al. | 568/565 |

*Primary Examiner*—Werren B. Lone
*Attorney, Agent, or Firm*—Oblon, Fisher, Spivak, McClelland & Maier

[57] ABSTRACT

Process for the preparation of araliphatic dihydroperoxides which comprises oxidizing a hydrocarbon of the formula:

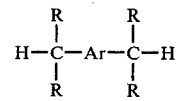

with oxygen or an oxygen-containing gas, (2) extracting the resulting dihydroperoxide with an alkali metal hydroxide solution of a concentration of 1–12% thereby producing an aqueous extract and an organic raffinate, (3) neutralizing any alkali metal hydroxide remaining in the organic raffinate with carbon dioxide, thereby producing alkali metal carbonate or bicarbonate in the raffinate, (4) washing the alkali metal carbonate or bicarbonate remaining in the raffinate with wash-water, (5) extracting from the wash-water used in step (4) any dissolved hydroperoxides remaining therein with a hydrocarbon solvent, and (6) optionally recycling the hydroperoxide-containing hydrocarbon solvent into the process. The resulting wash-water effluent is free of polluting and contaminating materials.

12 Claims, 2 Drawing Figures

PROCESS FOR THE PREPARATION OF ARALIPHATIC DIHYDROPEROXIDES

BACKGROUND OF THE INVENTION

1. Field of the Invention

This invention relates to a process for the preparation of araliphatic dihydroperoxides wherein the waste water produced therefrom contains a decreased amount of hydroperoxide fractions. Phenolic bodies are otherwise formed from these hydroperoxide fractions.

2. Brief Description of the Prior Art

It is known to oxidize di-tert.-alkyl substituted aromatic hydrocarbons of the formula

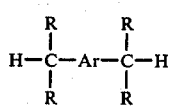

wherein Ar is an aromatic radical and R is an alkyl group, especially m- and/or p-diisopropylbenzene, with oxygen or oxygen-containing gases at elevated temperatures at for example a temperature range from 60°–120° C., to the corresponding dihydroperoxides of the formula:

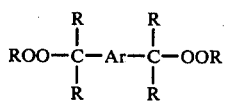

The most important chemical reactions which occur under oxidation conditions for m- and/or p-diisopropylbenzene (DIPB) are shown in the following reaction scheme:

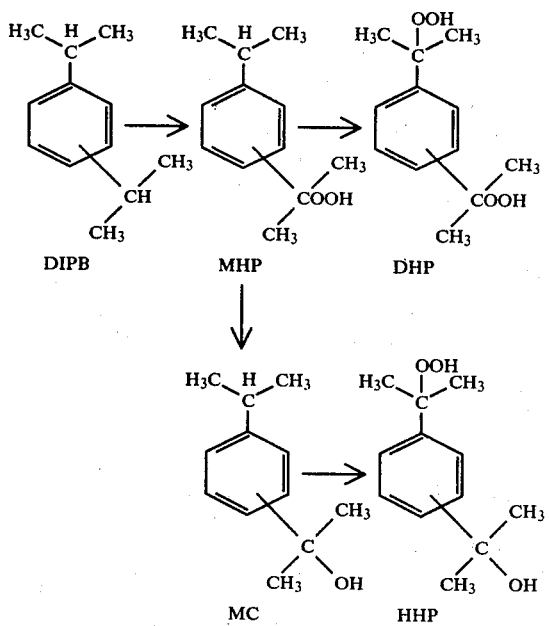

In this scheme is shown the oxidation of the hydrocarbon DIPB to the monohydroperoxide MHP, further oxidation of the MHP to dihydroperoxide DHP, the thermal and/or catalytic decomposition of the MHP to the monocarbinol MC and its further oxidation to the hydroxy hydroperoxide HHP. A goal of this technical process of the oxidation of di-tert. alkylated aromatics is in general, to isolate the dihydroperoxide (DHP) from the oxidation mixture, and then to treat the same according to well-known methods with mineral acids to catalyze the formation of the corresponding phenolic substances. In the case of DIPB, this catalytic reaction yields hydroquinone and/or resorcinol. The oxidation of the hydrocarbon, for example the m- and/or p-DIPB is in general, and among other things for safety precautions, only carried out to a predetermined conversion. At this stage, the oxidation mixture contains, besides of the unreacted hydrocarbon, relatively large amounts of the kinetic intermediate MHP and a relatively small amount of DHP and HHP.

It has been known for a long time that it is possible to extract DHP and HHP from the oxidation mixture with 1–12% of an aqueous alkaline metal hydroxide in selective fashion. After this extraction procedure, there remains behind as a raffinate, a mixture of unreacted hydrocarbon, such as for example DIPB, the intermediate MHP and also, in greatly decreased mass, DHP and HHP. However, there also fall into this organic mixture certain fractions in the free form of alkali metal hydroxides such as for example in solution or in an emulsion. When, as is obvious in a technical process, the mixture which is now poorer in DHP is recycled into the oxidation zone in order to produce more DHP, the free alkali metal hydroxide is also thereby recycled into the oxidation chamber. It is however known that the oxidative formation of hydroperoxides from araliphatic hydrocarbons takes place under most preferred conditions, i.e., with the highest possible yield of hydroperoxide, in mildly acidic or mildly basic media. This implies that if the alkali metal hydroxide-containing recycle solution after the extraction, is not after-treated, it would introduce strongly alkaline conditions into the oxidation reaction. It has therefore been proposed in DE-PS 1237118 that the alkali metal hydroxide present in the recycle be neutralized by treatment with gaseous $CO_2$ and then to eliminate the thus formed alkali metal carbonate or alkali metal bicarbonate with a water wash.

This method of operation is however associated with a disadvantage. If one carries out the process according to the aforementioned patent publication, one finds out that the wash-water has extracted from the recycle, besides of inorganic salts also certain fractions of hydroperoxides. The wash-water may thus contain a hydroperoxide content of 1–3% by weight. It is evident that such a water cannot be mixed with other water effluents of a chemical factory without objection, since it is known that it is possible to form unwanted phenolic bodies from the hydroperoxides contained therein. It is possible to find out from an analysis of the hydroperoxides contained in the effluent water that these comprise 85–95% of the valuable intermediate MHP, 4–10% of HHP and 1–5% of DHP.

The removal of MHP-constituent in the effluent water according to DE-PS 1237118 carries with it a decrease in the yield of the overall process of preparation of the dihydroperoxide, which will hereinafter be described in more detail, of 1–3% based on the starting DIPB.

SUMMARY OF THE INVENTION

It was therefore an object of the invention, to search, during the preparation of dihydroperoxides, for measures which would substantially prevent the contamination of the effluent water with hydroperoxides and simultaneously increase the overall yield of dihydroperoxides.

The object was solved by finding that the hydroperoxides could be extracted from the wash water at ordinary or elevated temperatures, such as for example, in the temperature range of 20°-60° C., with aliphatic or aromatic hydrocarbons, such as for example, the n- and iso- paraffin hydrocarbons in the C-range of 5-8, with benzene, toluene, ethylbenzene, cumene and other alkylated aromatics or with mixtures of such hydrocarbons.

It is therefore an object of the invention to provide a method of preparing araliphatic dihydroperoxides of the general formula:

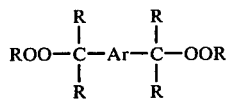

wherein Ar=aromatic radical and R=H or $C_1$-$C_4$ alkyl, by oxidation of a hydrocarbon of the formula:

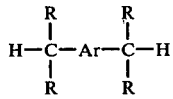

with oxygen or oxygen-containing gases, extracting the dihydroperoxides with 1-12% alkali metal lye as well as concomitant neutralization of the alkaline metal hydroxide remaining in the organic raffinate with $CO_2$, followed with a washing of the thus formed alkali metal carbonate with water, wherein the wash-water used for the alkali metal carbonate wash is, prior to discarding extracted of any dissolved hydroperoxide components with a hydrocarbon, and the thus extracted hydroperoxide components are optionally recycled into the process.

BRIEF DESCRIPTION OF THE PREFERRED EMBODIMENTS

The hydrocarbon media useful for extraction of the wash-water according to the present invention are themselves only sparingly soluble in the wash-water. The choice of the hydrocarbon useful for the extraction of the wash-water is purposely carried out so that from the resulting extract it is relatively simple to recover both the solvent itself and the hydroperoxides. A method of separation of these two components is by distillation of the solvent, whereby the hydroperoxide mixture falls out as the sump. Preferably, the distillation of the solvent is carried out in a vacuum still. Since hydroperoxides generally quickly decompose at temperatures higher than about 100° C., it is preferred to use during the extraction of the wash-water, a hydrocarbon with a low boiling point, preferably lower than 100° C., or in the case when a high boiling point medium is used, the distillation of the solvent is carried out in a vacuum still under reduced pressure.

In a particularly preferred embodiment, which underlines the great value of this invention, it is possible to use as the extraction medium, the di-tert.-alkyl substituted aromatics which are also used as starting materials in the oxidation reaction. In such case, the extract is united with the recycled stream without further process steps and the mixture is then returned to the overall process.

The extraction of the hydroperoxides from the wash-water coming from the oxidation-recycle stream according to the present invention may be carried out with the usual extraction apparatuses, such as for example a mixer- settler- apparatus. It is however, generally sufficient to bring the wash-water into a one time contact with the hydrocarbon-type extraction medium followed by settling of the phases, to result in a transfer of the hydroperoxide into the extraction medium. For example it is possible to decrease the hydroperoxide content in the wash-water from 1-3% by weight of 0.1-0.3% by weight, i.e., a 1/10 ultimate decrease in the original value. An aqueous stream with such low rest hydroperoxide content may be added without objections to the waste-water canals.

In the extraction of the present invention, the wash-water and the hydrocarbon are used in a weight ratio of between 1:1 and 10:1.

On the one hand, it is useful for the purpose of the possibly complete elimination of the hydroperoxides from the wash-water to use a relatively large excess of the extraction medium. On the other hand, from a practical technical point of view, this also results in that a large amount of extraction medium has to be recovered with a concomitant increase in cost. It is therefore, preferred to set the wash-water and extraction medium to a weight ratio of between 3:1 and 6:1.

If the choise is made to carry out the extraction according to the present invention with the hydrocarbon used as starting material for the oxidation reaction leading to dihydroperoxide, then it is possible without further steps to extract the hydroperoxides from the wash-water precisely with the exact amount of hydrocarbon which may then be directly added at the appropriate step in the technical overall process, to replace mole by mole the amount of produced dihydroperoxide. In other words, in the most preferred embodiment of the invention, the starting hydrocarbon can itself be used in the wash-water extraction without disturbing the overall mole balance of the technical cyclic process.

Having generally described this invention, a further understanding can be obtained by reference to certain specific examples which are provided herein for purposes of illustration only and are not intended to be limiting unless otherwise specified.

Figure 2:
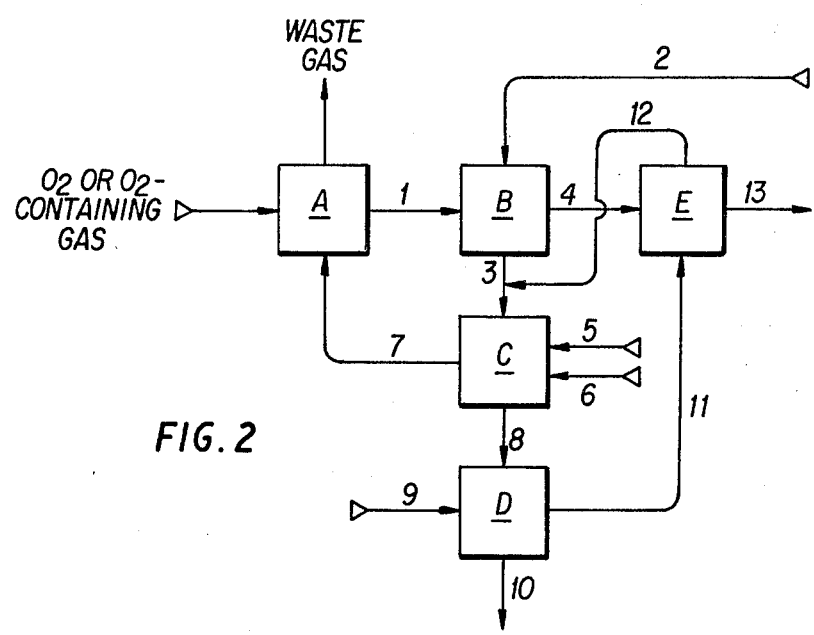

The block scheme of FIG. 1 describes the invention in its most general form while the block scheme of FIG. 2 shows the invention in a preferred embodiment of carrying out the oxidation of diisopropylbenzene to dihydroperoxide.

BLOCK DIAGRAM 1

Di-tert. alkyl-substituted aromatic hydrocarbon is oxidized with oxygen or oxygen-containing gas in oxidation reactor A, to the desired degree of conversion. The dihydroperoxides-containing oxidate is carried through line 1 into the extraction unit B, where it is extracted with 1-12% aqueous alkali metal lye which is introduced through line 2. While the dihydroperoxide-loaded lye is removed through line 4, the recycle is streamed through line 3 into the neutralization and wash unit C. The alkali metal hydroxides which are co-carried in the recycle are neutralized with $CO_2$ with enters through line 5, and the resulting carbonates are washed with water which enters through line 6. The recycle then streams through line 7 back into the oxidation reactor. The wash-water which has incorporated alkali carbonates and hydroperoxides from the recycle stream, flows through line 8 into the extraction unit D. It is here where the extraction of the hydroperoxides according to the present invention is carried out by hydrocarbon which enters through line 9, wherein the wash-water is intimately mixed with the hydrocarbon and the mixture is then allowed to separate into two phases. The wash water is then removed through line 10, containing only 0.1-0.3% by weight hydroperoxide. The hydroperoxide-loaded extraction medium is then carried through line 11 into a separation unit such as a distillation unit E. It is here where the extraction medium is stripped and recycled through line 9 to the extraction unit D, wherein any loss which is unavoidable in such a technical process is made up through line 13. The recovered hydroperoxides in unit E are united through line 12 with the recycle stream. A fresh amount of tert.-alkyl substituted aromatic hydrocarbon is optionally added through stream 14 to the recycle, or said starting material may be directly added to the oxidation reaction.

BLOCK DIAGRAM 2

The oxidate of the m- and/or p-DIPB leaves the oxidation reactor A through line 1 and flows into the extraction unit B. It is here where the extraction of the DHP and HHP occurs by introduction through line 2 of a stream of 1-12% aqueous alkali metal lye. The extraction lye which is now loaded with DHP and HHP and only very small amounts of MHP flows into the extraction unit E. The recycle which is poor in DHP and HHP is led through line 3 into the neutralization and wash unit C. $CO_2$ streams through line 5 into unit C for the neutralization of the co-carried alkali metal lye, and water streams through line 6 for the washing of the resulting alkali carbonates or bicarbonates. The carbonate-free recycle flows through line 7 back into the oxidation reactor A. The wash-water from line 6, now loaded with alkali metal carbonates and about 1.1% by weight of hydroperoxides flows through line 8 into the inventive extraction step D. The water phase is mixed herein with added DIPB which is flowed through line 9 into a mixing zone. The wash-water amount which is added through line 6 is measured in such a way that it stands in a weight ratio of 4.5 to 1 relative to the DIPB added through line 9. After passing through a settling zone, the newly separated two phases are removed through two lines. The wash water is removed through line 10, containing 0.17% by weight of hydroperoxides and is added to the waste water canal. The DIPB-phase which is now loaded with about 4.2% by weight of hydroperoxides, wherein 88% of these are MHP, flows through line 11 into the extraction unit E, into which the DHP- and HHP-loaded alkaline stream is also added through line 4.

After mixing and resettling of both streams in E, it is determined that the DIPB-phase gives up to the alkaline phase its small amount of DHP- and HHP-fractions and takes up otherwise from the alkaline phase, a MHP fraction. The alkaline phase now free of MHP leaves the unit E through line 13 to further processing. The DIPB-phase is reunited via line 12 with recycle stream 3. The DIPB-amount added through line 9 is then measured in such an amount that it corresponds exactly molarly to the sum of outflowing moles of DHP and HHP leaving through line 13.

Having now fully described this invention, it will be apparent to one of ordinary skill in the art that many changes and modifications can be made thereto without departing from the spirit or scope of the invention set forth herein.

What is claimed as new and intended to be secured by Letters Patent is:

1. In a process for the preparation of araliphatic dihydroperoxides of the formula:

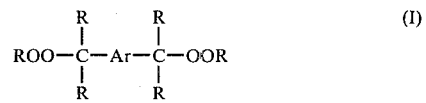

wherein Ar is benzene and R is hydrogen or a $C_1-C_4$ alkyl, the process comprising the steps of:
(1) oxidizing a hydrocarbon of the formula:

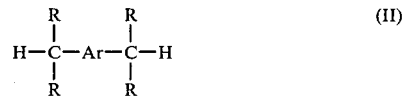

with oxygen or an oxygen-containing gas;
(2) extracting the resulting dihydroperoxide of formula (I) with an alkali metal hydroxide solution of a concentration of 1-12%, thereby producing an aqueous extract and an organic raffinate;
(3) neutralizing any alkali metal hydroxide remaining in said organic raffinate with $CO_2$ thereby producing alkali metal carbonate or bicarbonate in said raffinate; and
(4) washing the alkali metal carbonate or bicarbonate remaining in said raffinate with wash-water, the improvement which comprises:
(5) extracting from the wash water used in step (4) any dissolved hydroperoxides reamining therein with a hydrocarbon solvent.

2. The process of claim 1, wherein said hydrocarbon of formula (II) is selected from the group consisting of m- and p-diisopropylbenzene and mixtures thereof.

3. The process of any of claims 1 or 2 wherein said hydrocarbon solvent used in step (5) is substantially immiscible with said wash-water.

4. The process of claim 3, wherein said hydrocarbon solvent has a boiling point lower than 100° C.

5. The process of any of claims 1 or 2 wherein said hydrocarbon solvent is selected from the group consisting of $C_5-C_8$ aliphatic hydrocarbons, benzene and $C_1-C_4$ alkyl-substituted aromatic hydrocarbons.

6. The process of claim 5, wherein said $C_1-C_4$ alkyl-substituted aromatic hydrocarbons are selected from the group consisting of toluene, ethylbenzene and cumene.

7. The process of any of claims 1 or 2 which further comprises separating the solvent from said hydroperoxide-containing solvent; re-using said separated solvent in further extraction of wash-water; and recycling the recovered hydroperoxides into the process.

8. The process of claim 5 wherein the hydrocarbon solvent is the hydrocarbon of formula (II) and which further comprises recycling the used hydrocarbon solvent as the hydrocarbon in Step 1.

9. A process according to claim 8, wherein said hydrocarbon of formula II is used in a molar amount equal to the production of dihydroperoxide.

10. The process of any of claims 1 or 2, wherein the weight ratio of said wash water to said hydrocarbon solvents in step (5) is 1:1 to 10:1.

11. The process of claim 10, wherein said ratio is 3:1 to 6:1.

12. The process of claim 1 wherein the hydroperoxide containing hydrocarbon solvent from step 5 is recycled into the process.

* * * * *